(12) United States Patent
Overstreet (10) Patent No.: US 7,317,944 B1
(45) Date of Patent: Jan. 8, 2008

(54) SYSTEM AND METHOD FOR USING A MULTI-CONTACT ELECTRODE TO STIMULATE THE COCHLEAR NERVE OR OTHER BODY TISSUE

(75) Inventor: Edward H Overstreet, Valencia, CA (US)

(73) Assignee: Advanced Bionics Corporation, Valencia, CA (US)

( * ) Notice: Subject to any disclaimer, the term of this patent is extended or adjusted under 35 U.S.C. 154(b) by 342 days.

(21) Appl. No.: 10/886,801

(22) Filed: Jul. 8, 2004

Related U.S. Application Data (60) Provisional application No. 60/485,583, filed on Jul. 8, 2003.

(51) Int. Cl.
*A61N 1/08* (2006.01)
*A61B 5/00* (2006.01)

(52) U.S. Cl. ............................. 607/56; 607/55; 607/57; 600/559

(58) Field of Classification Search ............ 607/55–57, 607/137; 600/559; 381/60
See application file for complete search history.

(56) References Cited

U.S. PATENT DOCUMENTS

| | | | |
|---|---|---|---|
| 3,751,605 A | 8/1973 | Michelson | |
| 4,400,590 A | 8/1983 | Michelson | |
| 4,495,384 A | 1/1985 | Scott et al. | |
| 4,532,930 A | 8/1985 | Crosby et al. | |
| 4,819,647 A | 4/1989 | Byers et al. | |
| 5,344,387 A | 9/1994 | Lupin | |
| 5,603,726 A | 2/1997 | Schulman et al. | |
| 5,626,629 A | 5/1997 | Faltys et al. | |
| 5,824,022 A | 10/1998 | Zilberman et al. | |
| 5,938,691 A | 8/1999 | Schulman et al. | |
| 6,002,966 A | 12/1999 | Loeb et al. | |
| 6,052,624 A | 4/2000 | Mann | |

(Continued)

FOREIGN PATENT DOCUMENTS

WO  WO-03/015863 A2  2/2003

OTHER PUBLICATIONS

Overstreet and Faltys inventors for AB-254U; U.S. Appl. No. 10/218,645; filed Aug. 13, 2002; entitled "Cochlear Implant and Simplified Method for Fitting Same".

(Continued)

*Primary Examiner*—Carl Layno
*Assistant Examiner*—Tammie K Heller
(74) *Attorney, Agent, or Firm*—Philip H. Lee; Victoria A. Poissant (57) ABSTRACT

A system and method for preserving temporal and spatial resolution in complex sounds for poor performing patients having high stimulation thresholds is described. The system and method employs two or more adjacent electrode contacts to deliver concurrent stimulation. This concurrent delivery of stimuli creates a high current field intensity that overlaps between individual current fields generated by the two or more adjacent electrodes and which individual fields are summed to create an overlapping field that has a higher current field intensity than a single current emanating from an individual electrode. The use of this method reduces or eliminates the need to increase either the stimulus current amplitude or to increase the pulse width, both of which may cause loss of system resolution, i.e., loss of fine structure information that is used to resolve complex sounds such as music.

16 Claims, 10 Drawing Sheets

U.S. PATENT DOCUMENTS

| | | | |
|---|---|---|---|
| 6,067,474 | A | 5/2000 | Schulman et al. |
| 6,078,838 | A | 6/2000 | Rubinstein |
| 6,157,861 | A | 12/2000 | Faltys et al. |
| 6,195,585 | B1 | 2/2001 | Karunasiri et al. |
| 6,205,360 | B1 | 3/2001 | Carter et al. |
| 6,208,882 | B1 | 3/2001 | Lenarz et al. |
| 6,219,580 | B1 | 4/2001 | Faltys et al. |
| 6,249,704 | B1 | 6/2001 | Maltan et al. |
| 6,289,247 | B1 | 9/2001 | Faltys et al. |
| 6,295,467 | B1 | 9/2001 | Kollmeier et al. |
| 6,393,325 | B1 | 5/2002 | Mann et al. |
| 6,415,185 | B1 | 7/2002 | Maltan |

OTHER PUBLICATIONS

Faltys inventor for AB-257U; U.S. Appl. No. 10/218,616; filed Aug. 13, 2002; entitled "Bionic Ear Programming System".

Segel, Overstreet, Kruger, and Mishra inventors for AB-313U; U.S. Appl. No. 10/651,653; filed Aug. 29, 2003; entitled "System and Method for Fitting a Cochlear Implant Sound Processor Using Alternative Signals".

Overstreet inventor for AB-362U; U.S. Appl. No. 10/647,372; filed Aug. 25, 2003; entitled "Enhanced Methods for Determining Iso-Loudness Contours for Fitting Cochlear Implant Sound Processors".

Overstreet, Litvak, and Faltys inventors for AB-378U; U.S. Appl. No. 10/698,097; filed Oct. 31, 2003; entitled "Multi-Electrode Stimulation to Elicit Electrically-Evoked Compound Action Potential."

Overstreet inventor for AB-379U; U.S. Appl. No. 10/698,098; filed Oct. 31, 2003; entitled "Method and System for Generating a Cochlear Implant Program Using Multi-Electrode Stimulation to Elicit the Electrically-Evoked Compound Action Potential".

FIG. 8B

# SYSTEM AND METHOD FOR USING A MULTI-CONTACT ELECTRODE TO STIMULATE THE COCHLEAR NERVE OR OTHER BODY TISSUE

This application claims the benefit of U.S. Provisional Application Ser. No. 60/485,583, filed Jul. 8, 2003, which application is incorporated herein by reference in its entirety.

BACKGROUND OF THE INVENTION

The present invention relates to a system and method for using a multi-contact electrode to stimulate cochlear nerves or other body tissue. More particularly, the invention relates to systems and methods that use multi-channel cochlear nerve stimulation for stimulating individuals who have high stimulation thresholds.

Use of implantable cochlear stimulating devices for restoration of hearing is now a well-accepted modality for treating profound deafness. A cochlear implant system may be fully implantable or partially implantable. In a partially implantable device, there can be two components, an external component containing the battery and an implantable component which contains additional circuitry for processing the stimulation protocol. The implantable component usually consists of a stimulating cochlear lead with an array of multiple electrodes attached to the lead. The stimulating lead with the electrode array is inserted into the cochlea, for instance, into the tympanic chamber (scala tympani). After the electrode array is implanted into the cochlea, the electrodes may be stimulated one at time. In multi-channel systems having independent programmability for each electrode, different stimulus pulse amplitudes and, in some cases, pulsewidths may be delivered at two different electrodes in the same time interval.

The stimulation delivered by an electrode is generally a pulse or a series of pulses. The stimulus pulses are usually biphasic, i.e., the pulses may have a negative first phase and a positive second phase, where the positive second phase is also known as the recharge phase. The negative phase and positive phase are charge balanced to prevent over-accumulation of charges in the tissue adjacent to the stimulating electrode and also to prevent premature corrosion of the stimulating electrode. The negative first phase of the pulse has a time duration. This time duration is commonly referred to as the stimulus "pulse width". The pulse width as thus defined does not include the duration of the positive second phase.

The stimulation strength or level that just produces stimulation (or capture) of a nerve is termed a "stimulation threshold". In cochlear stimulation, the stimulation threshold also correlates closely to perception threshold since the firing of only a few ganglion cells (nerve fibers) can be discerned by an individual. To determine stimulation, a stimulus pulse width (pulse duration) is chosen and held constant, for example, 20 microseconds, while amplitude of the pulse is gradually increased. In one method of determining stimulation threshold, the stimulus amplitude is increased until the patient is able to perceive a sound. In an alternative method, the actual neural response (using neural response imaging), or the electrical conduction activity of a cochlear nerve that has been "captured", may be detected using a recording system when the stimulation threshold has been reached.

The stimulation threshold depends on at least two stimulus parameters: pulse amplitude and pulse duration (or pulse width). The stimulation threshold curve varies inversely between the pulse amplitude and pulse width. Such a threshold curve is also called a strength—duration curve. In accordance with this threshold curve, a larger pulse amplitude may compensate for a reduction in the pulse width to achieve threshold stimulation of a nerve. Alternatively, a larger pulse width can compensate for a smaller pulse amplitude to achieve threshold stimulation.

Normally, stimulation threshold for cochlear applications may be achieved using a stimulus setting of less than about a 50 microsecond pulse width and a current amplitude less than about 1 milliampere. In some poor performing patients, however, it may be necessary to increase the amplitude to the maximum compliance voltage allowed by the stimulator system. These particular patients may be poor performing for a number of reasons. One reason is that disease has caused many nerve cells in the cochlea to die. In addition, the patient may have a peculiar anatomical structure that causes the nerves to be located further away from the stimulating electrodes. As a result, the remaining viable nerves may be dispersed further away from a stimulating electrode and therefore be more difficult to isolate and stimulate.

Sound information is coded in the auditory system in at least two important ways. The first is temporal coding. Temporal information is conveyed as signal information that depends on the rate of firing (frequency) of a nerve fiber or cell. A stimulus may be repeated as a "pulse train" having a specific firing rate or frequency. The variation of stimulus frequency may be translated to frequency of electrical conduction in a specific nerve that is transmitted to the brain, which frequency variation can be perceived as temporal nuances in the sound. Coding of sounds also occurs spatially or spectrally with respect to the arrangement of ganglion cells (nerve fibers) along the cochlea (when the cochlea is viewed as unwound from its coiled state).

The electrode array has a set of electrodes that can be linearly spaced apart along the distal portion of a stimulating lead. As implanted in the cochlea, the electrode array may be placed adjacent to a particular set of cochlear nerve fibers which line the length of the cochlea (modiolus). The nerve fibers are located between the basal (opening) to the apical (tip) of the cochlea and are spatially coded such that certain sound frequencies preferentially stimulate nerve fibers located at the apical ends or the basal end of the cochlea. Thus, by choosing to stimulate through a specific set of electrodes along the cochlea, specific nerve fibers that code for specific sound frequencies can be stimulated. Loudness (intensity) of sound may be coded by recruiting increasing numbers of cochlear nerve fibers. Thus, a just perceptible or threshold sound may occur with stimulation of as few as 3 to 10 ganglion nerve cells, whereas to increase the perceived intensity of the sound, hundreds or even thousands of ganglion nerve cells must be recruited simultaneously.

The typical solution for stimulating a poor performing patient with high stimulation thresholds is to increase the amplitude of the stimulation until the patient reports an adequate loudness percept or until sufficient loudness is determined. A typical problem is that a patient encounters the stimulation output limits of the device before reaching the high stimulation levels necessary to achieve adequate loudness percept. The applied stimulation may be in the form of either voltage stimulation pulses or current stimulation pulses. The maximum available system stimulation level is reached when the voltage stimulation pulses or the current stimulation pulses cannot be increased further because a maximum compliance voltage of the stimulation device has been reached. The maximum compliance voltage is termed the system "compliance voltage." Increasing the stimulation amplitude, however, can be an inadequate solution because, at such high amplitudes, any "headroom" or extra stimulus amplitude that permits a greater dynamic range of loudness is eliminated. That is, in order to maintain a greater dynamic range of loudness, it is desirable to provide stimulation levels below the system compliance voltage.

In addition, increasing the stimulus amplitude enlarges the current field spread and reduces the spatial specificity or selectivity of an electrode to stimulate sets of nerve fibers because the larger current fields between electrodes tend to overlap or "smear" into other spatial regions containing adjacent sets of nerves during different time intervals. A set of nerves may therefore be stimulated by more than a single electrode, at slightly different times, resulting in a "smearing" effect.

Another way of increasing the stimulus strength is to increase the pulse width. Unfortunately, however, as the pulse width is increased, the temporal information becomes reduced because the wider pulse durations limit the maximum rate of stimulation frequency. Generally, a shorter pulse width can operate at a higher stimulus frequency (pulses per second).

The overall effect therefore in having to increase amplitude or pulse width is to lower the resolution of perceived sound.

It would thus be desirable to have a method of stimulation that can mitigate the resulting loss of information in poor performing patients.

What is needed, therefore, is an improved method of stimulating the auditory nerves, or other tissue being stimulated, that retains temporal and/or spectral information for poor performing patients with high stimulation requirements.

SUMMARY OF THE INVENTION

The present invention addresses the above and other needs by providing a stimulation system and method that retains temporal resolution and, to a lesser degree, spatial resolution.

In one aspect of the invention, a method is provided for cochlear stimulation of patients with high stimulation threshold. The method comprises: providing a cochlear stimulation system that includes an array of electrode contacts E1 ... EN, wherein the number of electrode contacts N is at least 2, and wherein each electrode contact is independently programmable; measuring a stimulation threshold including pulse width and pulse amplitude for at least one of the electrode contacts; determining whether the measured stimulation threshold represents a high stimulation threshold; and stimulating at least two adjacent electrodes concurrently with stimulus currents $I_1$ and $I_2$, when the measured stimulation threshold represents a high stimulation threshold. $I_1$ and $I_2$ are current amplitudes emanating from electrode E1 and E2, respectively, which current amplitudes may be the same or different. If different, current steering may be advantageously implemented. Because the two currents may be different, it is preferable that the cochlear stimulation system have the capability to provide independently programmable stimulation channels so that the stimuli delivered concurrently through each electrode in the array may be programmed individually for pulse width and pulse amplitude.

In one embodiment of the method, the step of predetermining whether a high stimulation threshold exists in a poor performing patient can be based on, for instance, the application of a pulse width that is about 50 microseconds and has an amplitude that exceeds 80% of the maximum system compliance voltage. The stimulation threshold may be determined by asking a patient to indicate when a sound is first perceived while the stimulus strength is increased gradually stepwise. Alternatively, the stimulation threshold may be determined automatically by the cochlear implant system using a neural response imaging system that can sense the resulting cochlear nerve action potential after a suprathreshold stimulus is applied.

In another embodiment, a method of is provided for preserving temporal and spatial resolution in complex sounds for poor performing patients having high stimulation thresholds. The method comprises: providing a patient with an implantable cochlear stimulator (ICS), the ICS having means for programmably providing stimulus currents through selected multiple electrode contacts on an electrode array adapted to be inserted into the cochlea of the patient; determining whether a patient exhibits a high stimulation threshold; and for those patients exhibiting a high stimulation threshold, simultaneously stimulating two or more adjacent electrode contacts on the electrode array in order to deliver concurrent stimulation to the cochlea, wherein the concurrent delivery of stimuli creates an overlapping field that has a higher current field intensity than a single current emanating from an individual electrode contact, and further wherein the concurrent delivery of stimuli reduces or eliminates the need to increase either the stimulus current amplitude or to increase the stimulus pulse width, either of which may cause loss of fine structure information that is used to resolve complex sounds.

In another aspect of the invention, a system is provided for preserving temporal and spatial resolution in complex sounds for poor performing patients having high stimulation thresholds. The system comprises: an implantable cochlear stimulator (ICS), the ICS having means for programmably providing stimulus currents through selected multiple electrode contacts on an electrode array adapted to be inserted into the cochlea of the patient; means for determining whether a patient exhibits a high stimulation threshold; and means for simultaneously stimulating two or more adjacent electrode contacts on the electrode array in order to deliver concurrent stimulation to the cochlea for those patients exhibiting a high stimulation threshold; wherein the concurrent delivery of stimuli creates an overlapping field that has a higher current field intensity than a single current emanating from an individual electrode contact, and further wherein the concurrent delivery of stimuli reduces or eliminates the need to increase either the stimulus current amplitude or to increase the stimulus pulse width, either of which may cause loss of fine structure information that is used to resolve complex sounds.

The delivery of concurrent stimuli from adjacent electrodes in the electrode array has the effect of summing the current fields to increase the intensity of the summed activation field in the overlap region. The summing of fields produces a current field intensity that is greater than the individual current field intensities emanating from any single electrode, E1 ... EN. By thus summing the current fields, the need to boost the stimulus (pulse) current amplitude or the pulse width can be eliminated and hence can circumvent the loss of temporal resolution that accompanies these compensating tactics. Consequently, substantial sound resolution may be retained in a poor performing patient in addition to producing adequate sound loudness.

It is thus a feature of the present invention to provide a method of stimulation in poor performing patients with high stimulation levels, which method utilizes a multi-channel stimulator, having multiple electrodes and independently programmable channels without sacrificing compliance voltage headroom.

It is a further feature of the invention to preserve temporal resolution in poor performing patients.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Before describing the present invention, it will be helpful to review the operation of a typical cochlear stimulation system.

Multi-channel stimulators are used in various implantable medical devices. For example, such multi-channel stimulators can be found in spinal cord stimulation devices for treating intractable pain and cochlear devices for restoration of hearing in the profoundly deaf. As an exemplary application of the present invention, the invention will be discussed in the context of use in a cochlear implant device. Details associated with the operation of a typical cochlear implant system may be found in one or more of the following U.S. patents, each of which is incorporated herein by reference: U.S. Pat. Nos. 6,157,861; 6,002,966; 5,824,022; 5,603,726; 5,344,387; and 4,532,930.

Figure 1:
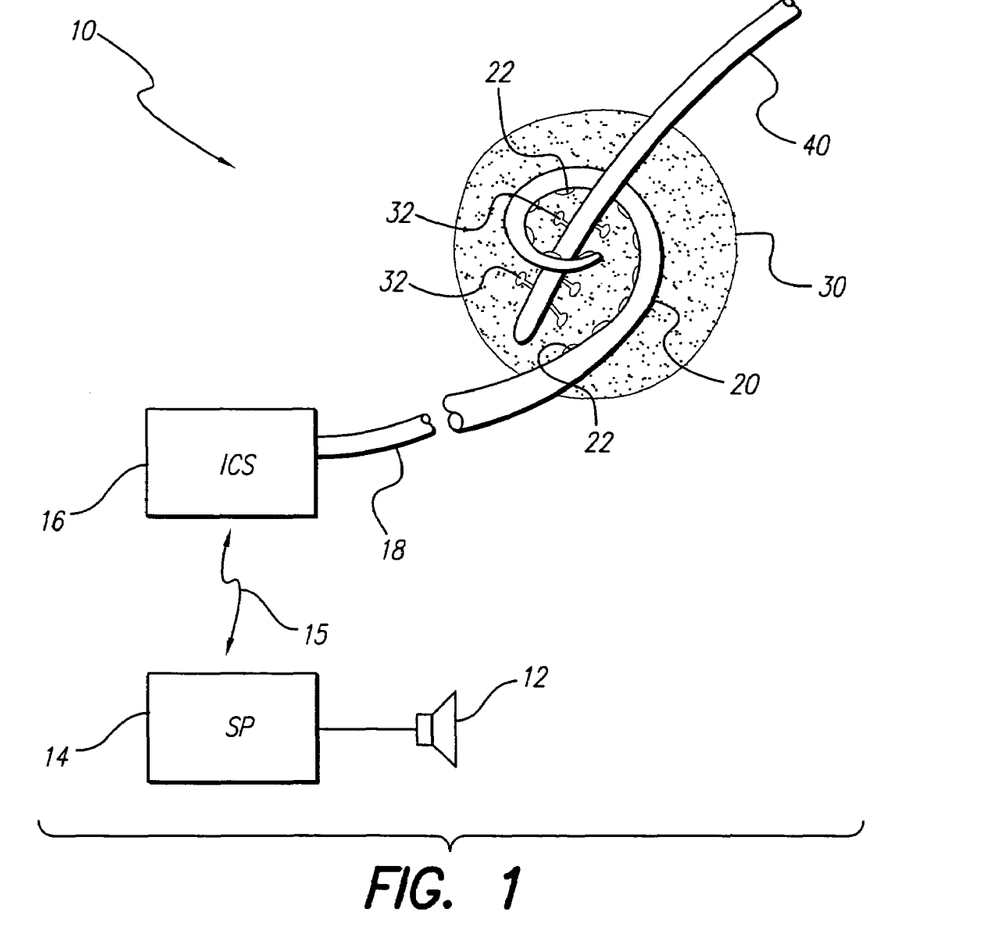
FIG. 1 shows, in accordance with the present invention, an illustration of one embodiment of the cochlear lead with an electrode array for modiolar placement.

FIG. 1 shows an illustration of one embodiment of the cochlear lead with an electrode array for modiolar placement.

A representative cochlear stimulation system 10 is illustrated in FIG. 1. A microphone 12 senses acoustic waves and converts such sensed waves to an electrical signal. The electrical signal is then processed in an appropriate manner by a speech processor (SP) 14. Such processing may include dividing the signal into different frequency bands and generating an appropriate stimulation control signal for each frequency band. The stimulation control signal(s) is passed on to an implantable cochlear stimulator (ICS) 16 via a radio-frequency communications link 15. The ICS 16 is connected to an electrode array 20. The electrode array 20 is inserted into a cochlea 30. (Note, that the representation of the cochlea 30 shown in FIG. 1 is meant only as a schematic representation.)

The electrode array 20 includes a plurality of spaced-apart electrode contacts 22 thereon. Each electrode contact 22 is electrically connected to the electrical circuitry within the ICS 16 by way of respective electrical wires 18 embedded within the electrode array 20 as is known in the art. The ICS, in response to the control signal(s) received from the SP 14, generates an electrical stimulation current on selected groupings of the electrode contacts 22.

The cochlea 30, as is known in the art, comprises a snail-shaped member having three parallel ducts that spiral around its center bony region, known as the modiolus. One of the spiraling parallel ducts within the cochlea is the scala tympani. The center bony region, or modiolus, is where ganglion nerve cells 32 are located. Each of the ganglion cells 32 is coupled to the auditory nerve 40, which connects to the brain.

It is the function of the cochlear stimulation system 10 to electrically stimulate the ganglion cells 22 with electrical stimulation current representative of the acoustic waves sensed by the microphone 12. In order to achieve this function, the electrode array 20 is inserted into the scala tympani so that the electrode contacts 22 encircle the modiolus and ganglion cells 32. Electrical stimulation current flows between selected electrode contacts 22 and hence stimulates the ganglion cells 32 near the selected electrode contacts, as controlled by the ICS 16 in accordance with a programmed or selected speech processing strategy. The speech processing strategy is defined by the control signals received from the SP 14. The control signals are modulated by the acoustic waves sensed by the microphone 12, thereby causing the stimulation current to stimulate appropriate ganglion cells as a function of the sensed acoustic waves. For example, low frequency acoustic waves cause ganglion cells near the apical tip of the cochlea to be stimulated, whereas high frequency acoustic waves cause ganglion cells near the basal region of the cochlea to be stimulated.

Stimulation of the ganglion cells can be accomplished using two electrode configuration modes. One electrode configuration mode is a "bipolar mode," which uses two electrode contacts 22 positioned relatively close to each other. In this mode, the load resistance appears between the two electrode contacts 22. The load resistance is made up of the interface between the tissue and electrode contacts 22 and the tissue itself between the electrode contacts.

Another electrode configuration is a "monopolar mode," which employs one of the electrode contacts 22 in the electrode array and an indifferent electrode that is relatively distant from the electrode contacts 22. In some cases, the indifferent electrode can be the exterior container (the "case") of the ICS, which container can be made from a biocompatible, electrically conductive metal such as titanium. In the monopolar electrode configuration, the load resistance is made up of the interface between the electrode contact 22 and tissue, the interface between the indifferent electrode and tissue, and the tissue itself between the electrode contact and the indifferent electrode. Because the monopolar electrodes are spaced far apart, with more tissue between the electrodes, the monopolar load resistance tends to be much higher than the bipolar load resistance.

In either the monopolar or bipolar electrode configuration mode, there are two stimulus modes that may be used: a uniphasic stimulus mode and a biphasic stimulus mode. A uniphasic stimulus mode provides current flow in only one direction through an electrode. A biphasic stimulus mode, however, provides current flow in both directions through an electrode within a relatively short time period. It is thought that uniphasic stimulation may cause electrical charge to accumulate in the tissue near the stimulating electrode and thereby cause injury to this tissue. In addition, it is also believed that uniphasic stimulation can cause premature degradation of the electrodes. Therefore, most conventional multi-channel stimulators, including ones for cochlear stimulators, typically use some form of biphasic stimulation.

Figure 2:
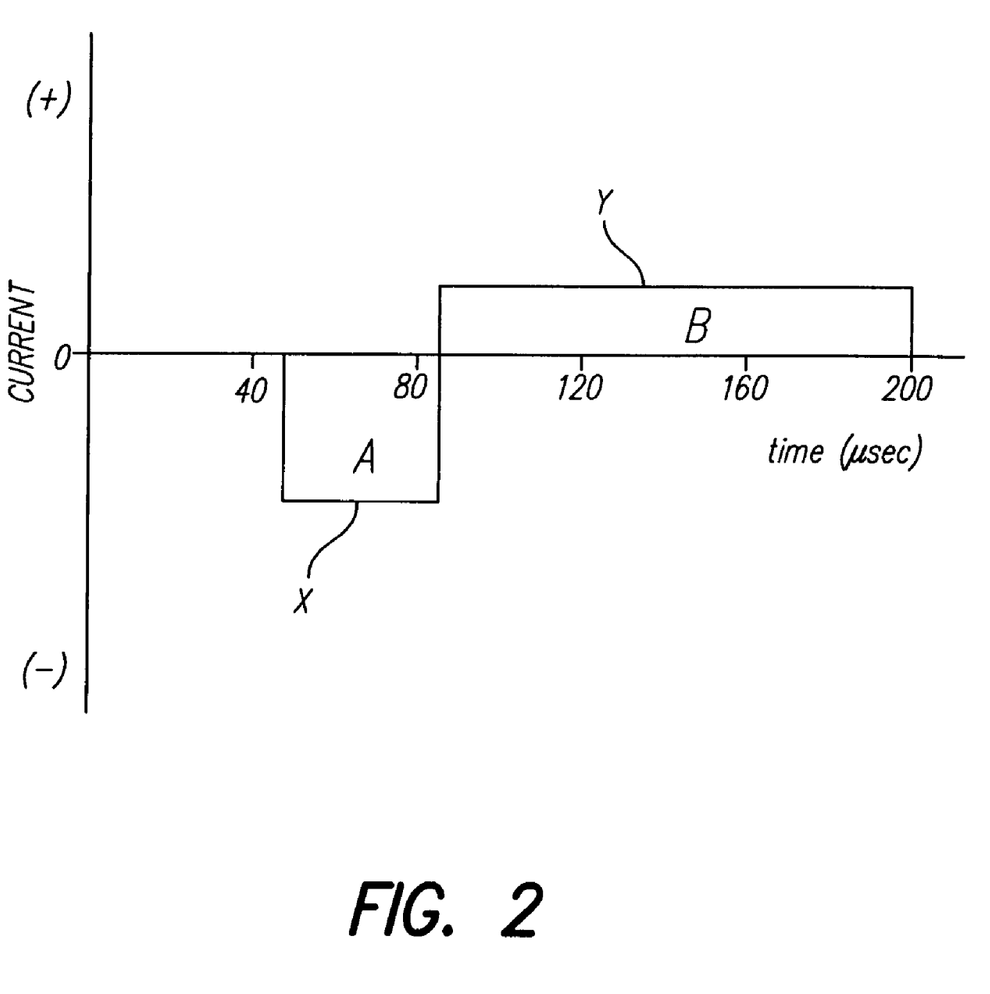
FIG. 2 shows, a biphasic stimulus, showing the negative (stimulating) phase of the stimulus and a positive recharge phase of the stimulus.

FIG. 2 shows a biphasic stimulus waveform as a function of time. The biphasic pulse consists of a negative phase X of the stimulus and a positive, "recharge" phase Y of the stimulus. Stimulus pulse waveforms X and Y are individually uniphasic. But considered together, they are biphasic because the flow of stimulation current through an active electrode is in both directions. A particular biphasic stimulation in which an equal quantity of electrical charge flows in both directions through an electrode is termed a "charged-balanced," biphasic stimulation. A charge-balanced stimulation can be achieved by ensuring that the flow of charge in both directions through a stimulating electrode is equal over time. As represented in FIG. 2, the accumulation of charge is represented by the area (A) and area (B) below and above the zero current flow line, respectively. In the waveform shown in FIG. 2, the areas below and above the zero line should be equal over a short period of time in order to achieve charge balancing. Such charge balancing is believed to prevent injury to cells which are near the stimulating electrode and, furthermore, prevent the stimulating electrode from degrading prematurely. For these reasons, conventional, multi-channel stimulators for cochlear implants and spinal cord stimulation generally employ charged-balanced stimulation regimes.

Figure 3:
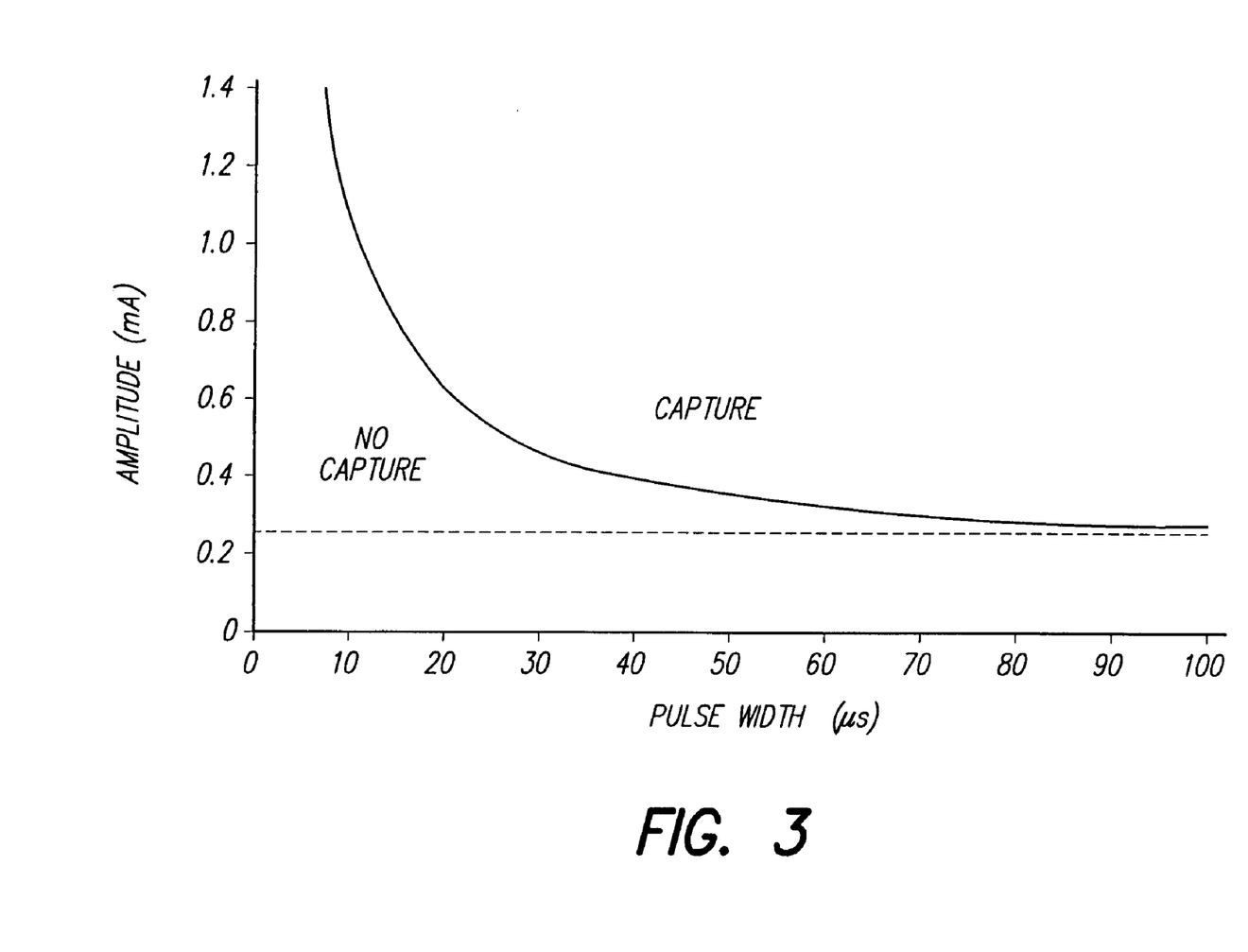
FIG. 3 shows, a typical strength-duration curve, wherein the curve provides the threshold stimulus required as paired data points of stimulus amplitude and pulse width.

FIG. 3 shows a typical strength-duration curve, wherein the X-Y pairs of points on the curve represent the threshold stimulus curve. The threshold stimulus is that stimulus (X,Y pair) that just fires (or captures) a target nerve. The X-axis represents the stimulus pulse width and the Y-axis represents the stimulus amplitude. It can be seen from the curve that when a narrow or short duration pulse width is used, the stimulus amplitude must be increased. If a larger pulse width is used, the stimulus amplitude may be made smaller. Thus, the stimulus pulse width and amplitude vary inversely.

Figures 4, 5:
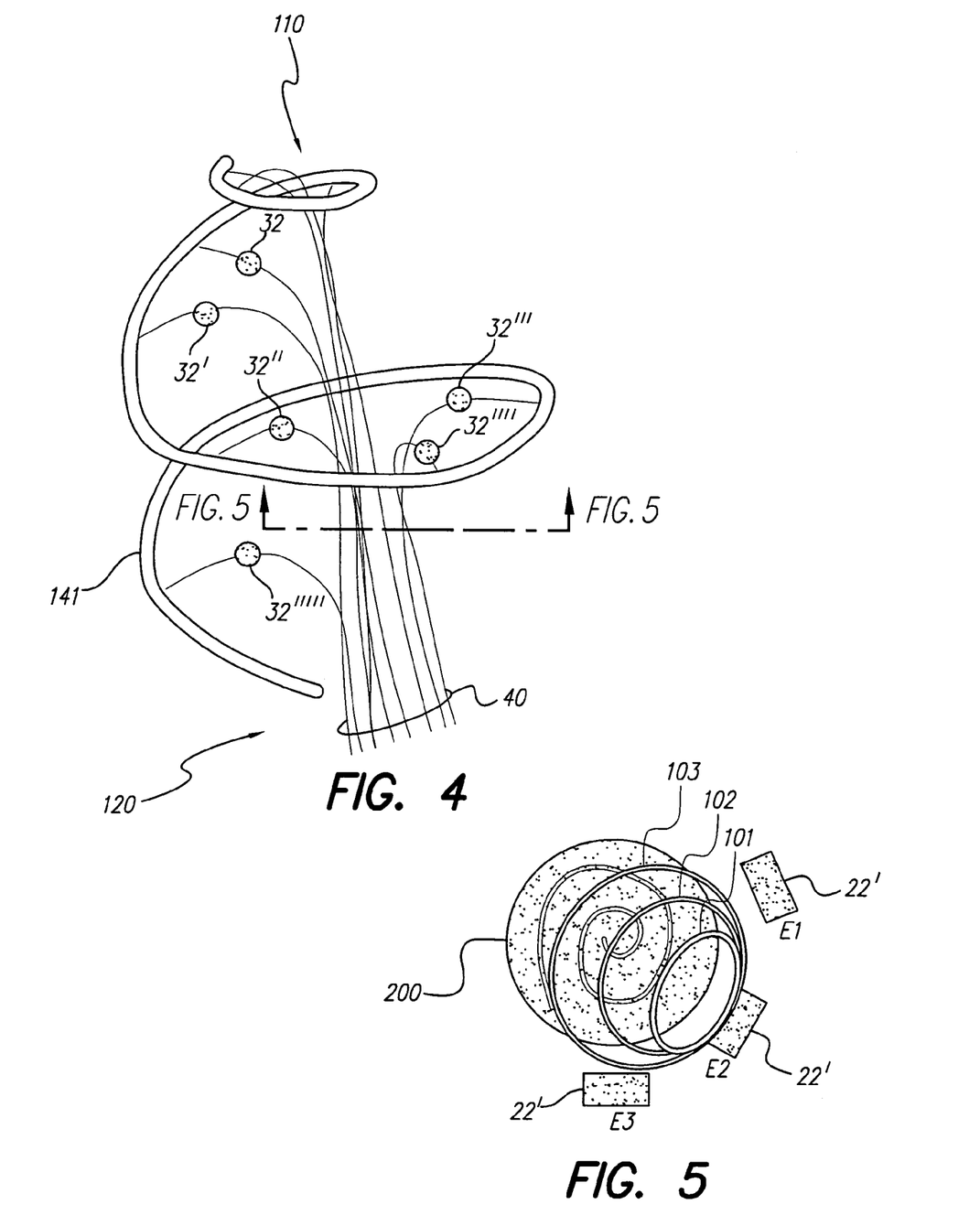
FIG. 4 shows a transverse (apical to basal) view of a cochlear nerve and branching ganglion cells.
FIG. 5 shows a sectional view at line FIG. 5-FIG. 5 of FIG. 4, showing a modiolus surrounded by electrodes.

FIG. 4 shows a transverse (apical to basal) view of the cochlear nerve 40 and its ganglion cells (nerve fibers) 32, 32', 32", 32'", 32"" and 32""'. The spiral line 141 indicates the spiral pathway of the lead and the approximate placement of the electrode array inside the cochlea. The circles 32, 32', 32", 32'", 32"" and 32""' shown in FIG. 4 represent the ganglion cells, and indicate points of the nerve fibers that may be stimulated by the electrodes. The higher frequencies are spatially (spectrally) mapped to the outer circumference of the modiolus and toward the basal end 40. The apical portion 110 of the cochlea (modiolus) and regions near the cochlear nerve spatially map the lower frequencies in the audible sound spectrum.

FIG. 5 shows a sectional view of the modiolus at the location of line FIG. 5-FIG. 5 of FIG. 4 (although FIG. 4 does not actually show the edges of the modiolus). An exemplary, three electrode array, having electrodes E1, E2 and E3, is shown wrapped around the cochlear nerve. FIG. 5 also shows stimulus current field lines 101, 102 and 103 for a current applied to electrode contact E2. Such current field lines indicate current spread at different intensity levels. In most patients a threshold current $I_{threshold}$, e.g., corresponding to stimulus current field line 101, may be sufficient to stimulate or capture a ganglion cell in the cochlea. In poor performing patients, however, who have fewer viable nerve fibers, it may be necessary to increase the stimulus strength to a value $I_{poor}$, e.g., corresponding to stimulus current field line 103. As represented qualitatively in FIG. 5 by the current field lines 101 and 103, $I_{poor}$ is significantly greater than $I_{threshold}$ in order to capture enough nerve fibers to be perceived as sound by the poor performing patient.

The stimulus strength may be increased by increasing the amplitude of the stimulus current, increasing the stimulus pulse width or increasing both the stimulus amplitude and pulse duration. In accordance with the stimulation threshold strength-duration curve for a ganglion nerve cell, these two parameters may be adjusted to compensate for a deficiency in the other. Increasing the stimulus amplitude broadens or widens the activation area in which nerves are present. Similarly, the activation field may be broadened, to an extent, by increasing the pulse duration (pulse width). Some nerves within the current field will have higher thresholds and may require even a greater stimulus strength to elicit stimulation (capture). Because poor performing patients have fewer viable nerve ganglion cells in any one area, it is often necessary to increase the stimulus strength to recruit or capture other nearby viable ganglion cells and to achieve adequate loudness perception. However, as a result of having to increase stimulus strength, spatial specificity may also be lost in poor performing patients.

Figure 6A:
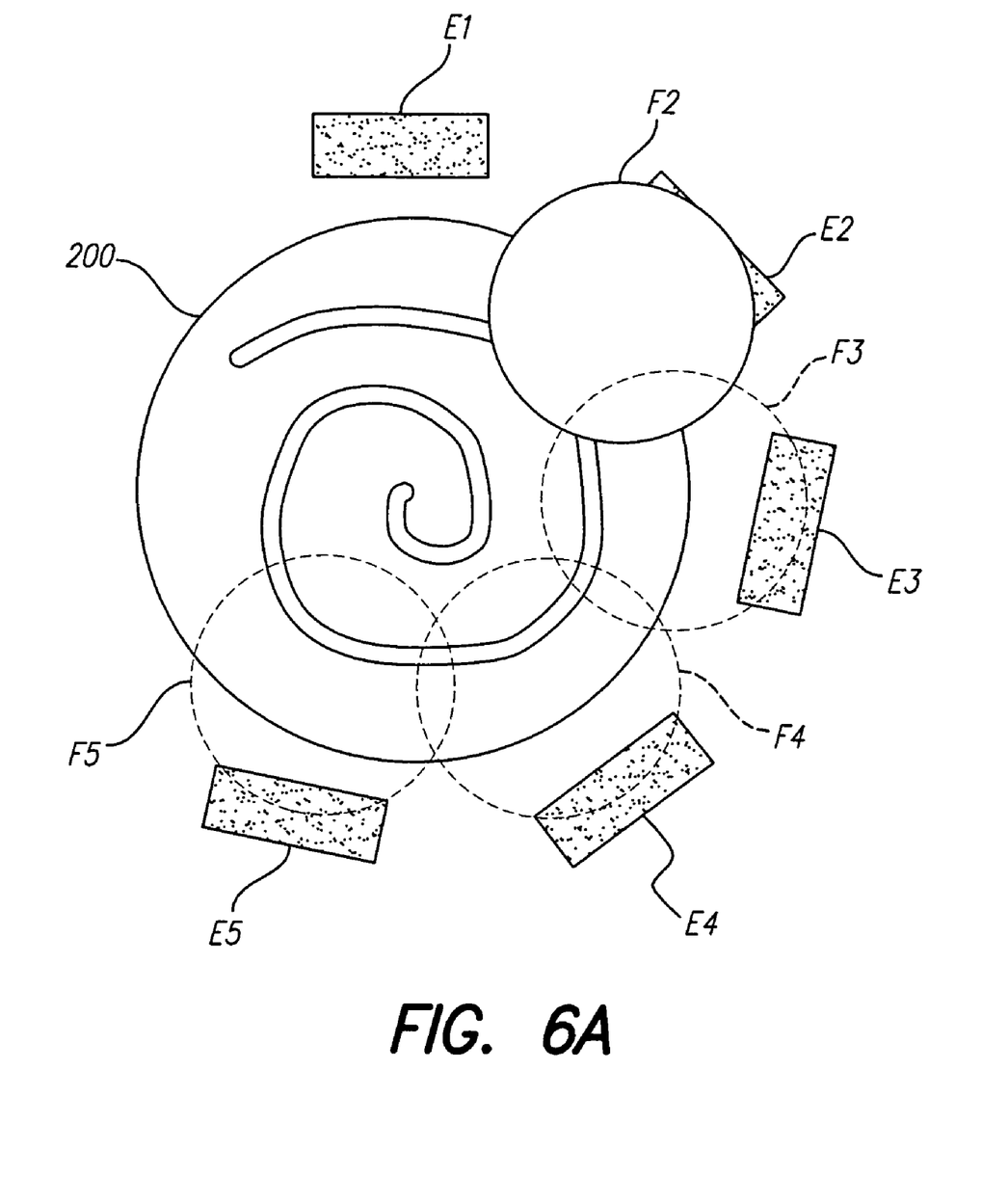
FIG. 6A shows a sectional view of a modiolus and a surrounding electrode array with activation fields in a normal performing patient.

FIG. 6A illustrates a cross-sectional area of the modiolus 200 and electrode array that is placed in the cochlea in a normal performing patient. The electrode array, in this particular example, has five electrode contacts E1, E2, E3, E4 and E5 which are spaced equally apart along the distal tip of a stimulation lead (not shown). Because the stimulation lead is placed inside the scala tympani, the electrodes are also equally spaced therein. The activation field of a single electrode contact E2 is represented by field F2. Similarly, electrode contact E3 has activation region F3, electrode contact E4 has activation region F4, and electrode contact E5 has activation region F5. A similar activation field, not shown, exists corresponding to electrode contact E1. It is emphasized that each of these activation fields occupies a space in the cochlea which is offset transversely (perpendicularly) to the plane represented by the sectional view of FIG. 6A because the lead inside is implanted in a spiral pathway and hence electrode contacts E1 . . . E5 are not in the same plane. It is also important to note that the region of activation for each electrode only minimally overlaps and encroaches upon the region of activation for an adjacent electrode. In one type of cochlear stimulation system, only one electrode in the set of electrode contacts, E1 through E5, is stimulated at any one time. It can be seen that as each electrode delivers a stimulus, essentially different populations or sets of nerve fibers within each activation field, for a given stimulus strength, are stimulated at any one time. When stimulation thresholds are low, as in a normal performing patient, the regions of activation for each electrode are distinct.

However, in the case of a poor-performing, high-threshold patient, it may be necessary to increase the amplitude of the current delivered at each electrode contact. Unfortunately, increasing the stimulus strength also makes the activation field associated with one electrode contact encroach into the activation field of another adjacent electrode contact, resulting in "smearing" of the spectral resolution.

Figure 6B:
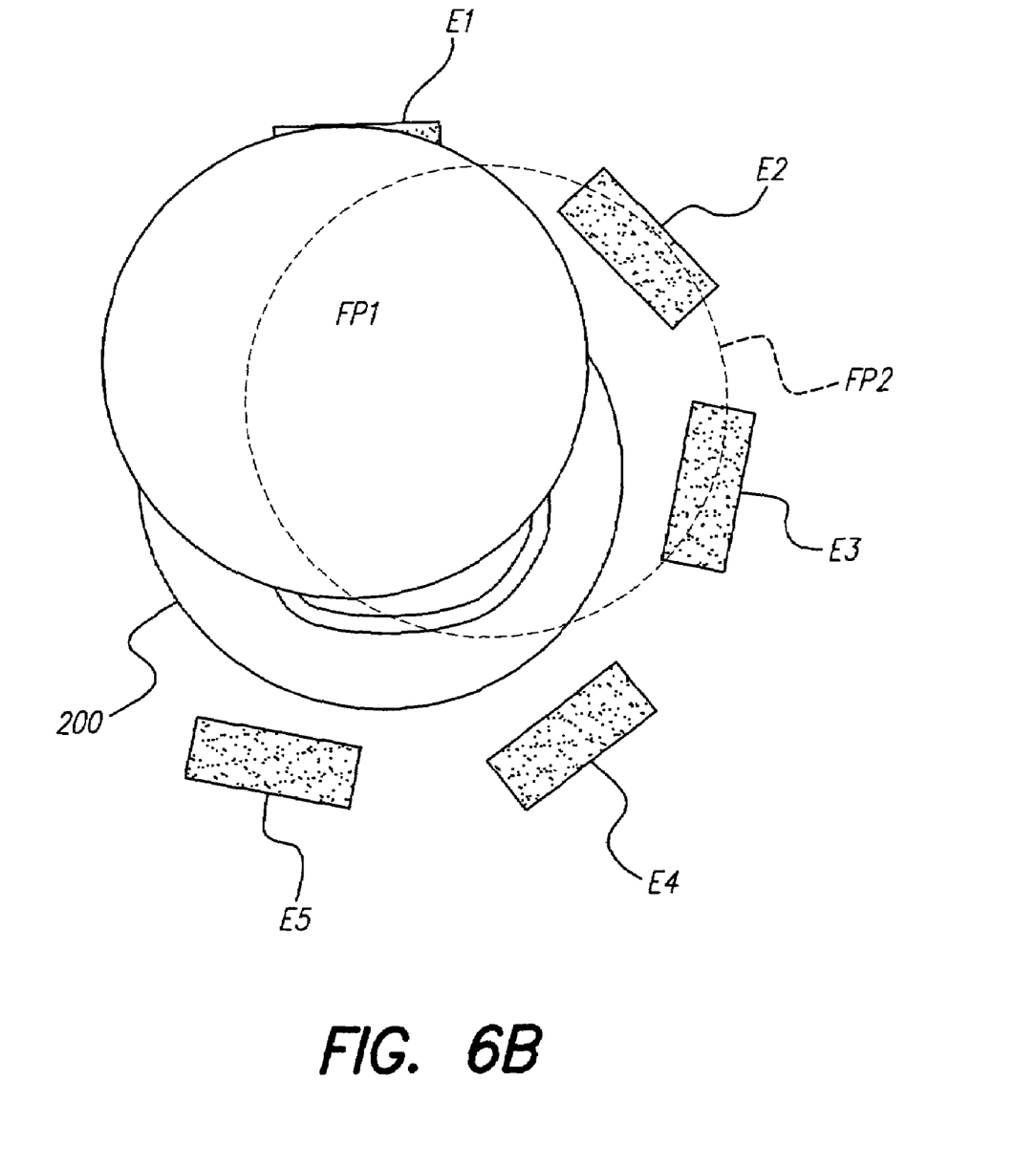
FIG. 6B shows a sectional view of a modiolus and a surrounding electrode array with larger activation fields needed for a poor performing patient.

FIG. 6B depicts a modiolus 200 and the same electrode array, E1 . . . E5, as in FIG. 6A, except in a poor performing patient. In such a patient, the current activation field FP1 (activation Field of Poor performer from E1) is larger than normal. Thus, in order to achieve sound perception in the poor performer, it is necessary to stimulate a wider region in order to capture enough viable nerve ganglion cells (nerve fibers) within the wider region. As a result, the activation field for any adjacent pair of electrodes overlap, for example, E1 (FP1) and E2 (FP2). Similarly, the activation fields will overlap between E2 (FP2) and E3 (FP3), between E3 (FP3) and E4 (FP4) and between E4 (FP4) and E5 (FP5). Therefore, as each electrode contact from E1 to E5 provides a stimulus pulse, in sequence, in different time intervals, certain populations of nerve cells or fibers will be stimulated, sequentially, resulting in a smearing effect and a loss of spatial (spectral) resolution.

Fine structure information in sounds which are coded both spectrally and temporally in the auditory system are necessary to distinguish complex sounds such as music. In poor performers, the spatial resolution can be diminished because using the larger regions of field activation result in less spatial specificity. Often, in poor performers, the stimulus amplitude must be increased to the maximum limit of the system compliance voltage. In other cases, the available compliance voltage may be simply insufficient to produce an adequate sound perception. In such cases, the stimulus strength may be further increased by increasing the pulse width. Such a compensating strategy, unfortunately, can degrade temporal resolution (on top of the already reduced spatial resolution) because use of large stimulus pulse widths prevents the coding of high frequency information. Thus, in poor performing patients, both spectral and temporal resolution may be degraded.

Figure 7A:
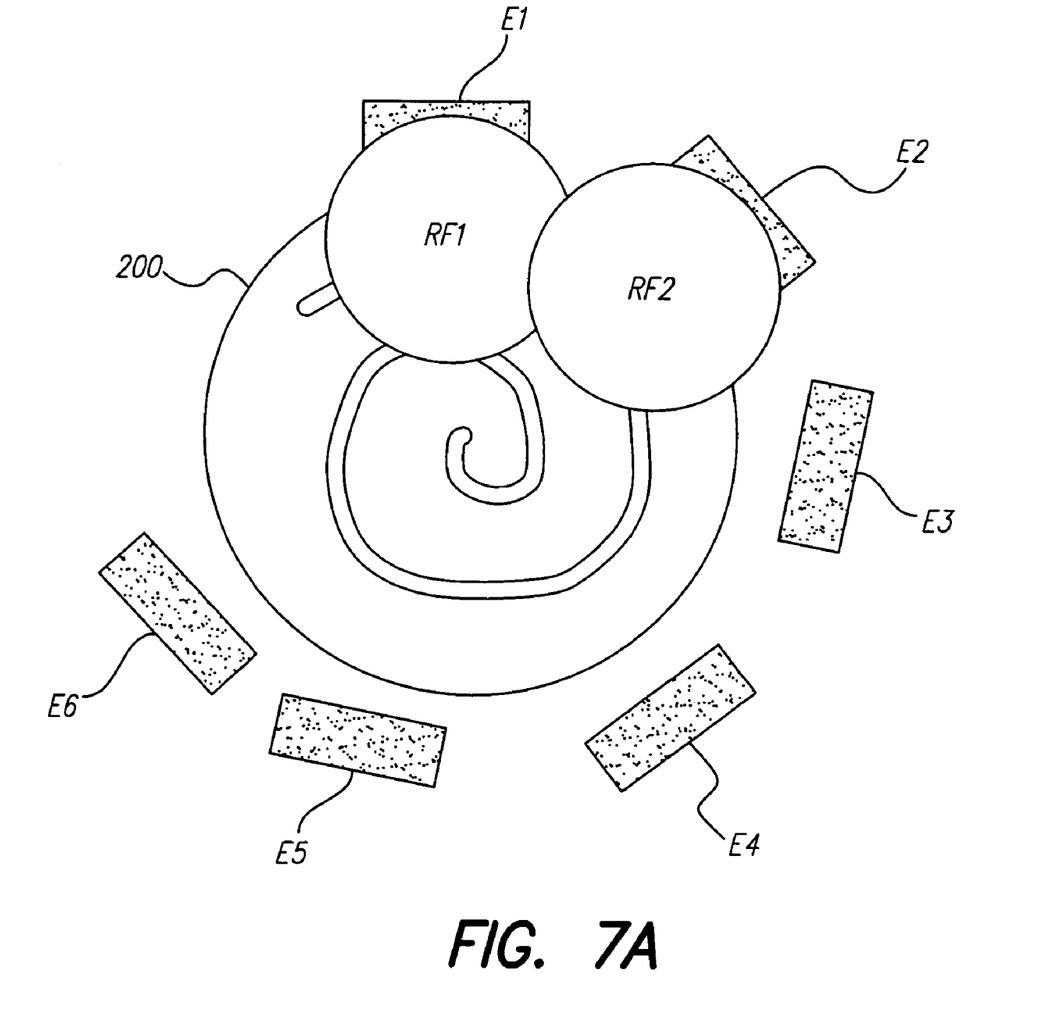
FIG. 7A shows, in accordance with the present invention, the multi-electrode method of stimulation for use in a poor performing patient, which method employs two adjacent electrodes delivering concurrent stimuli.
Figure 7B:
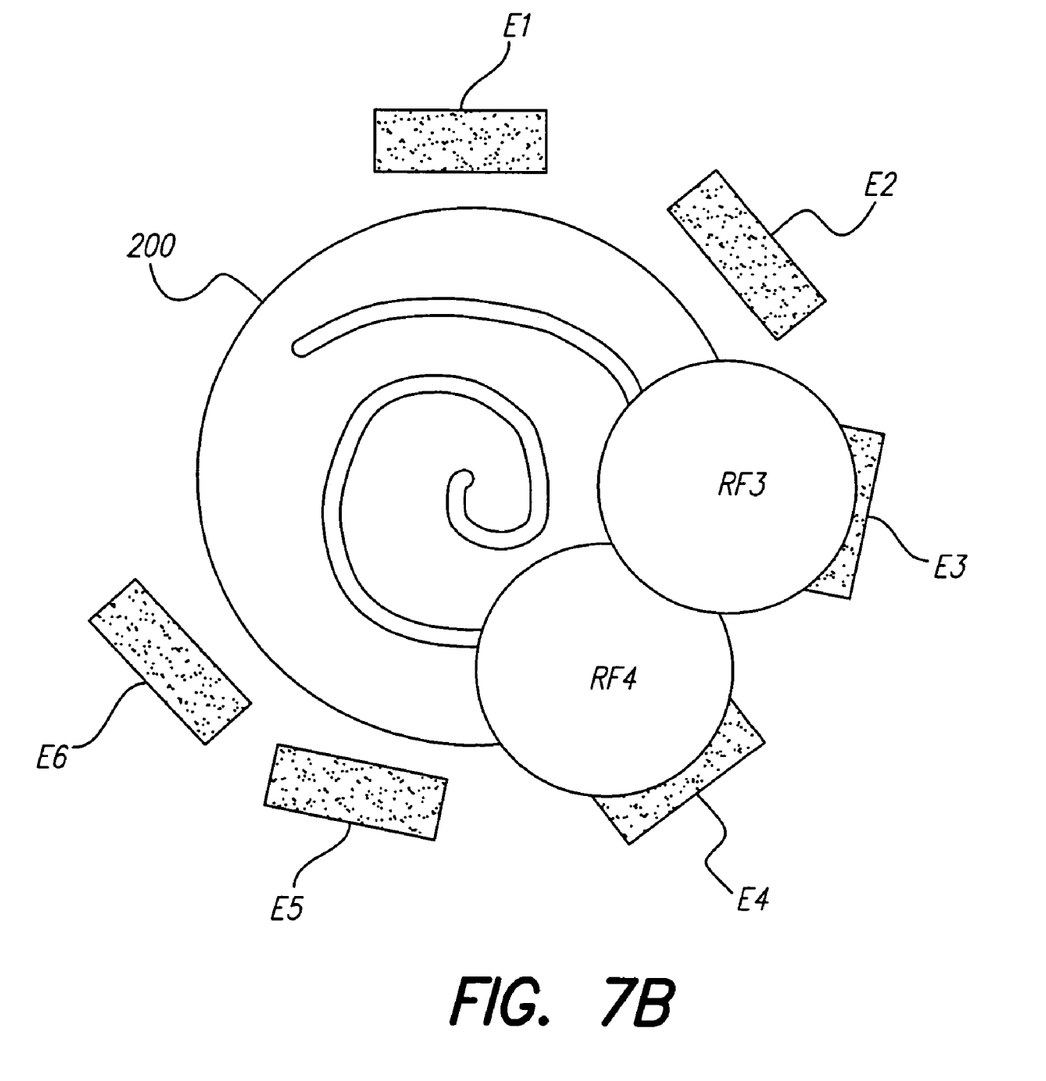
FIG. 7B shows, in accordance with the present invention, another view of the multi-electrode method showing activation fields for two different adjacent electrodes.

FIGS. 7A and 7B show, in accordance with the present invention, the method of stimulation for a poor performing patient. The method employs at least two electrodes to deliver concurrent stimuli and the method helps to preserve temporal and, to some extent, spatial specificity.

FIG. 7A illustrates, in accordance with the present invention, the method of stimulation which uses two adjacent electrode contacts, e.g., E1 and E2, that concurrently deliver stimuli in one time interval. In this example, current activation fields RF1 and RF2 are applied concurrently in a poor performing patient. The current fields RF1 and RF2 are summed and the summed activation field has greater intensity than the individual fields, RF1 and RF2. Consequently, a lower compliance voltage may be used to provide adequate sound perception in poor performing patients. It can be seen that the activation field created by such summation may be more restricted in its effective space than either the individual activation fields, RF1 or RF1. In the simplest form of the present method, the current emanating from electrode contacts E1 and E2 may be same. In that case, the overlapping activation field will be located somewhere between RF1 and RF2. In another embodiment of the method of the present invention, the stimulus amplitudes can be different at each electrode contact. For example, there may be two different current amplitudes $I_1$ and $I_2$. Such differential, simultaneous delivery of currents at adjacent electrodes can provide current steering such that the overlapping activation field can be deliberately steered closer to one of the activation fields, RF1 or RF2, so that a particular region and, hence, a particular set of ganglion cells can be stimulated.

FIG. 7B shows activation fields RF3 and RF4. Thus, in one embodiment of the present method, stimulation may occur in the following time sequence: in the first time interval, E1 and E2 can concurrently deliver a stimulus; in second time interval, E3 and E4 can concurrently deliver a stimulus; and in a third time interval, E5 and E6 can concurrently deliver a stimulus. In yet another embodiment, E1, E2, E3 and E4 can all deliver stimuli simultaneously.

An important advantage of the present method is that temporal resolution of the system can be preserved because the pulse width does not have to be increased. Because the pulse width does not have to be increased and small pulse widths may be used, e.g., 30 microseconds, the temporal specificity is preserved. While using two electrodes does decrease spatial specificity, on the other hand, it is an acceptable trade-off because the current may be steered. In addition, the spread of activation field with two electrodes can result in less smearing than a single electrode having a large field. Certainly, dynamic headroom can be preserved, effectively doubling the system compliance voltage. Because both temporal specificity and, to some degree, spectral specificity are preserved with the present stimulation method, fine structure information can be retained and conveyed.

Figure 8A:
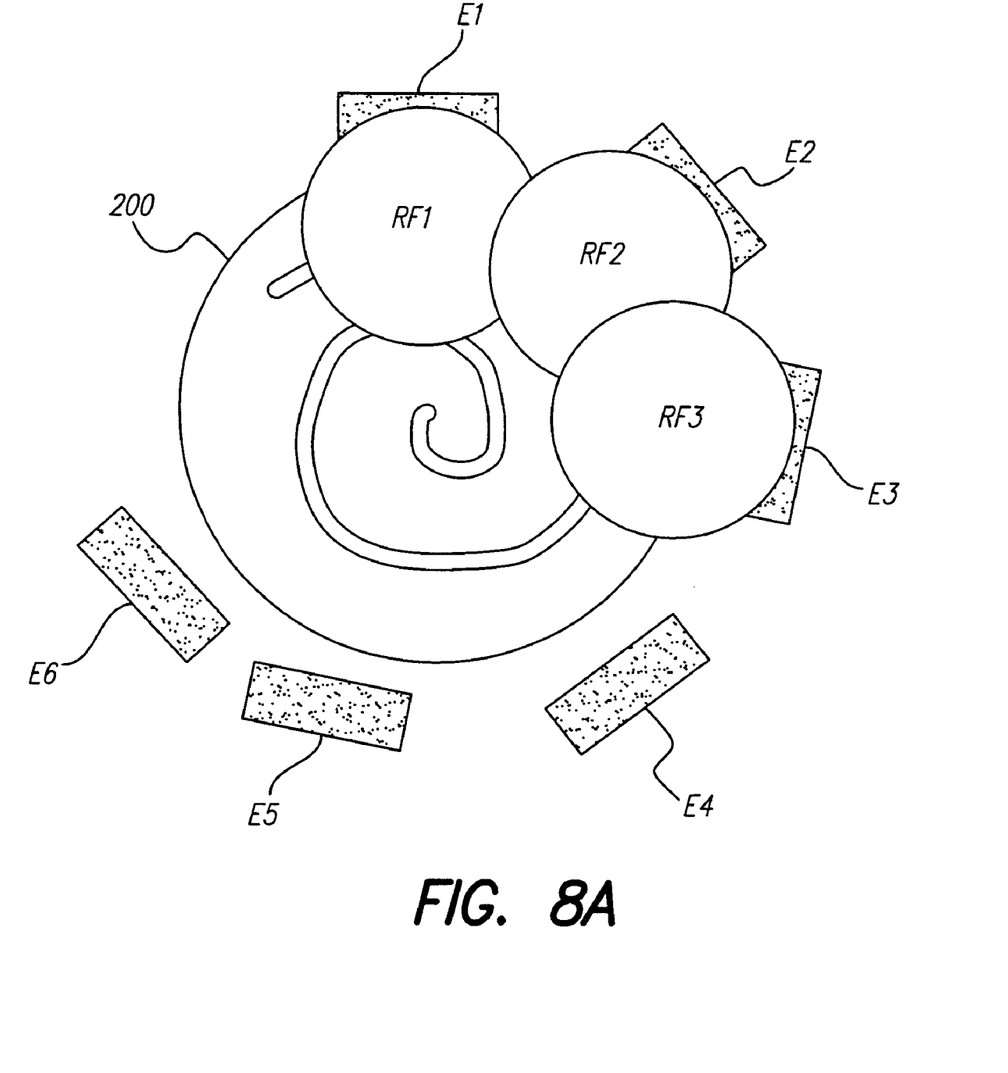
FIG. 8A shows, in accordance with the present invention, the method of stimulation using three adjacent electrodes.

FIG. 8A shows that the present method can be logically extended to simultaneous stimulation at three adjacent electrode contacts, e.g., E1, E2 and E3, in which the three overlapping current fields RF1, RF2 and RF3 create a summated activation field $F_{sum}$, which can have a higher field intensity than any individual component field and can be located somewhere near RF2.

Figure 8B:
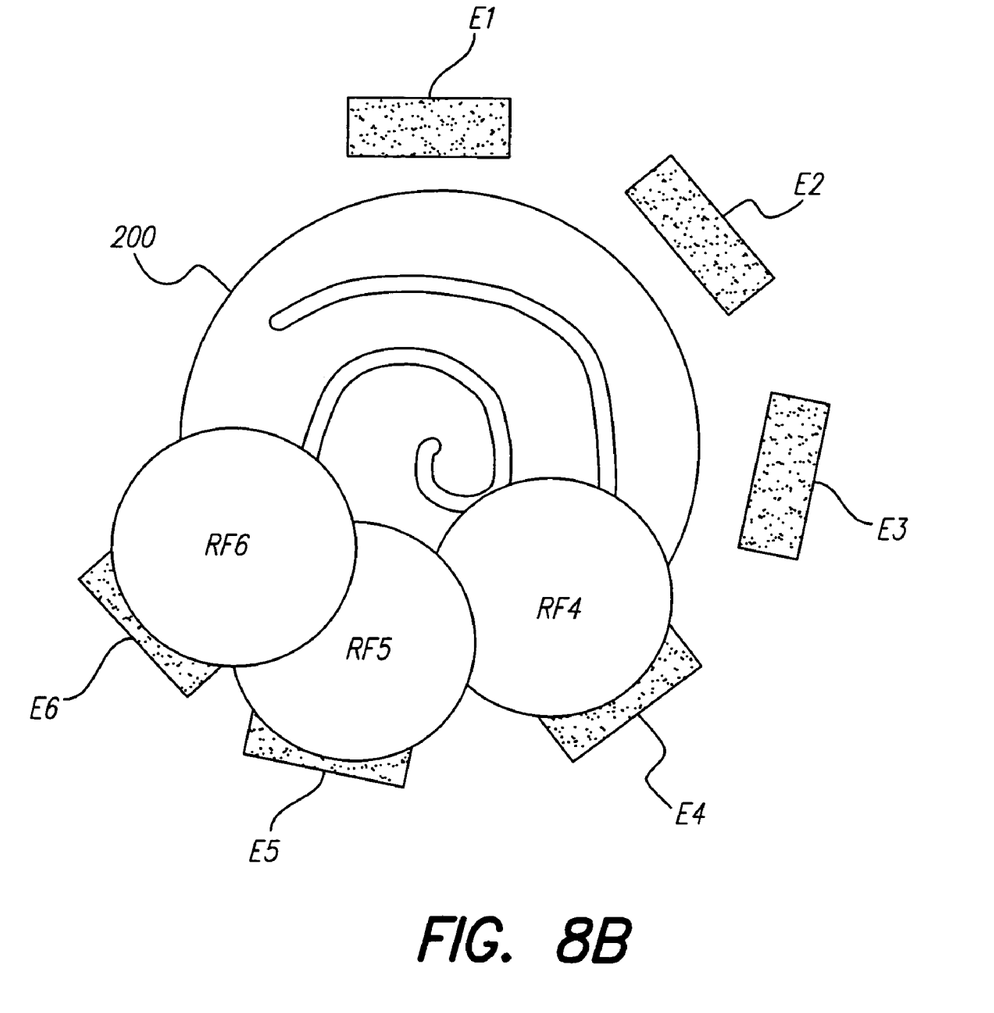
FIG. 8B shows, another view of the present method, using three different, adjacent electrodes which are stimulated concurrently.

FIG. 8B shows another set of three electrode contacts E4, E5 and E6 that may simultaneously deliver stimuli to produce activation fields RF4, RF5, and RF6, respectively. The stimulus amplitude emanating from any individual electrode E4, E5 or E6 is much less than an equivalent amplitude emanating from a single electrode.

Thus, in operation, whenever a poor performing patient is identified such that the current amplitude settings exceeds a predetermined level, e.g., 80% of the compliance voltage of the system, the present method calls for delivering concurrent stimulation from at least two adjacent stimulating electrode contacts. By so doing, the temporal and spatial resolution can be preserved using lower stimulus amplitudes and by keeping pulse width small. In accordance with the present invention, a set of two, three or four adjacent electrodes may be stimulated concurrently in a single time interval to achieve current summation. The multiple electrode contacts, in essence, when stimulated simultaneously, act as a single, large electrode contact, having an activation field that is preferentially nearer to the electrode contacts.

The effectiveness of the present invention has been demonstrated in the laboratory. Given that a stimulus strength of Xs microamperes delivered through a single electrode contact results in a loudness ranking of R, the equivalent loudness ranking R may be achieved using the method of the present invention, by using a stimulus strength that is only Xs/N, where N is the number of adjacent electrodes concurrently delivering the stimulus Xs. N can be a whole number representing up to four adjacent electrodes. This generalization assumes a stimulation configuration in which all electrodes concurrently deliver stimuli having equal energy, i.e., the same amplitude and pulse width.

Thus, as one example, when a 400 microampere stimulus is delivered as a biphasic pulse having a duration of 32 microseconds/phase on electrode contact E1, a loudness ranking of 6 (on a 1-10 arbitrary scale) is realized. In accordance with the present invention, when concurrent stimulation is applied through adjacent electrode contacts E1 and E2 with a biphasic stimulus pulse width of 32 microseconds/phase, and a stimulus amplitude of 200 microamperes, an equivalent loudness ranking of 6 is achieved. As shown by this example, the effective system voltage compliance is doubled, albeit at the expense of using more electrode contacts and therefore reducing some spectral specificity. Nevertheless, this is an acceptable trade-off since temporal resolution can be retained and system compliance voltage (dynamic headroom) can be increased.

Previous techniques of increasing pulse width for poor performing patients can significantly reduce the temporal information in addition to the loss of spatial specificity due to smearing. In contrast, the present method maintains greater temporal information by effectively increasing the available voltage compliance and by obviating the need to increase the pulse width.

While the invention herein disclosed has been described by means of specific embodiments and applications thereof, numerous modifications and variations could be made thereto by those skilled in the art without departing from the scope of the invention set forth in the claims.

What is claimed is:

1. A method of cochlear stimulation for patients with high stimulation thresholds, comprising:
    providing a cochlear stimulation system that includes an array of electrode contacts E1 . . . EN, wherein the number of electrode contacts N is at least 2, and wherein each electrode contact is independently programmable;
    measuring a stimulation threshold including pulse width and pulse amplitude for at least one of the electrode contacts;
    determining whether the measured stimulation threshold represents a high stimulation threshold; and
    stimulating at least two adjacent electrodes concurrently with stimulus currents $I_1$ and $I_2$, when the measured stimulation threshold represents a high stimulation threshold; and
    wherein determining whether the measured stimulation threshold represents a high stimulation threshold comprises determining whether the pulse width exceeds about 50 microseconds and the pulse amplitude exceeds about 80% of a system compliance voltage.

2. The method of claim 1, wherein measuring the stimulation threshold comprises obtaining feedback from patient perception.

3. The method of claim 1, wherein measuring the stimulation threshold comprises automatically measuring the stimulation threshold using a neural response imaging system that includes means for sensing evoked cochlear nerve action potentials in response to application of a supramaximal stimulus.

4. The method of claim 1, wherein the stimulus currents $I_1$ and $I_2$ are about equal in amplitude.

5. The method of claim 1, wherein the stimulus currents $I_1$ and $I_2$ are different in amplitude.

6. The method of claim 1 wherein the stimulus currents $I_1$ and $I_2$ comprise biphasic stimulus currents, having a first phase and a second phase.

7. The method of claim 6 wherein at least a portion of the first phase of stimulus currents $I_1$ and $I_2$ overlap in time.

8. The method of claim 1, wherein the number of electrode contacts N does not exceed 4.

9. A method of cochlear stimulation for patients with high stimulation thresholds, comprising:
    providing a cochlear stimulation system that includes an array of electrode contacts E1 . . . EN, wherein the number of electrode contacts N is at least 2, and wherein each electrode contact is independently programmable to be stimulated with a stimulation pulse having a programmed level, and further wherein a maximum stimulation level of the stimulation system is limited by a compliance voltage of the cochlear stimulation system;
    measuring a stimulation threshold including pulse width and pulse amplitude for at least one of the electrode contacts;
    determining whether the measured stimulation threshold represents a high stimulation threshold, wherein the high stimulation threshold comprises one wherein the measured stimulation threshold exceeds a predetermined level relative to the compliance voltage of the stimulation system; and
    when the measured stimulation threshold represents the high stimulation threshold, simultaneously stimulating at least two adjacent electrodes; and
    wherein determining whether the measured stimulation threshold represents a high stimulation threshold comprises determining whether the pulse width exceeds about 50 microseconds or the pulse amplitude exceeds about 80% of the system compliance voltage.

10. The method of claim 9, wherein measuring the stimulation threshold comprises obtaining feedback from patient perception.

11. The method of claim 9, wherein measuring the stimulation threshold comprises automatically measuring the stimulation threshold using a neural response imaging system that includes means for sensing evoked cochlear nerve action potentials in response to application of a supramaximal stimulus.

12. The method of claim 9, wherein the simultaneous stimulation of at least two adjacent electrodes comprises stimulating the at least two adjacent electrodes with respective stimulus currents that are approximately equal in amplitude.

13. The method of claim 9, wherein the simultaneous stimulation of at least two adjacent electrodes comprises stimulating the at least two adjacent electrodes with respective stimulus currents that are different in amplitude.

14. The method of claim 9 wherein the simultaneous stimulation of at least two adjacent electrodes comprises stimulating the at least two adjacent electrodes with respective stimulus currents that comprise biphasic stimulus currents, having a first phase and a second phase.

15. The method of claim 14 wherein at least a portion of the first phase of the respective stimulus currents overlap in time.

16. The method of claim 9, wherein the number of electrode contacts N does not exceed 4.

* * * * *